(12) United States Patent
Barrett

(10) Patent No.: US 9,717,903 B1
(45) Date of Patent: Aug. 1, 2017

(54) ELECTRONIC PROCESS TO RESTORE, IMPROVE AND/OR STRENGTHEN THE LIBIDO; METHOD TO MEND THE SEX DRIVE IN MALES AND FEMALES

(71) Applicant: Gary Barrett, Eatontown, NJ (US)

(72) Inventor: Gary Barrett, Eatontown, NJ (US)

( * ) Notice: Subject to any disclaimer, the term of this patent is extended or adjusted under 35 U.S.C. 154(b) by 0 days.

(21) Appl. No.: 14/660,876

(22) Filed: Mar. 17, 2015

(51) Int. Cl.
  A61N 1/02 (2006.01)
  A61N 1/04 (2006.01)
  A61N 1/18 (2006.01)
  A61N 1/36 (2006.01)

(52) U.S. Cl.
  CPC .................... A61N 1/36014 (2013.01)

(58) Field of Classification Search
  None
  See application file for complete search history.

(56) References Cited

U.S. PATENT DOCUMENTS

| | | | |
|---|---|---|---|
| 4,521,421 A * | 6/1985 | Foreman | C07D 471/04 514/267 |
| 4,550,733 A | 11/1985 | Liss et al. | |
| 4,586,509 A | 5/1986 | Liss et al. | |
| 4,614,193 A | 9/1986 | Liss et al. | |
| 4,614,866 A | 9/1986 | Liss et al. | |
| 4,724,835 A | 2/1988 | Liss et al. | |
| 4,784,142 A | 11/1988 | Liss et al. | |
| 5,109,847 A | 5/1992 | Liss et al. | |
| 5,421,817 A | 6/1995 | Liss et al. | |
| 5,450,845 A | 9/1995 | Axelgaard | |
| 5,487,759 A | 1/1996 | Bastyr et al. | |
| 5,514,175 A | 5/1996 | Kim et al. | |
| 5,571,149 A | 11/1996 | Liss et al. | |
| 5,776,170 A | 7/1998 | MacDonald et al. | |
| 5,785,040 A | 7/1998 | Axelgaard | |
| 5,851,223 A | 12/1998 | Liss et al. | |
| 5,990,078 A | 11/1999 | Toran-Allerand | |
| 6,161,044 A | 12/2000 | Silverstone | |
| 6,391,922 B1 * | 5/2002 | Fogel | A61K 31/00 514/702 |
| 6,898,465 B2 | 5/2005 | Gadsby et al. | |
| 6,941,171 B2 * | 9/2005 | Mann | A61N 1/36007 128/898 |
| 6,964,643 B2 * | 11/2005 | Hovland | A61F 5/48 601/6 |

(Continued)

FOREIGN PATENT DOCUMENTS

WO   WO2014/140832   * 9/2014

OTHER PUBLICATIONS

•Waldinger et al. Successful Transcutaneous Electrical Nerve Stimulation in Two Women with Restless Genital Syndrome: The Role of A_- and C- Nerve Fibers, Journal of Sex Med Mar. 2010; 7(3): 1190-9.*

(Continued)

Primary Examiner — Brian T Gedeon
(74) Attorney, Agent, or Firm — Cooper & Dunham LLP

(57) ABSTRACT

Methods to restore and/or improve the libido, the sex drive, in males and females, without introducing any external unnatural drugs. The process utilizes a TENS/EMS (Transcutaneous Electrical Nerve Stimulation/Electronic Muscle Stimulation) machine to naturally generate the increased production by the human body's nerve fiber's neurotransmitters.

22 Claims, 3 Drawing Sheets

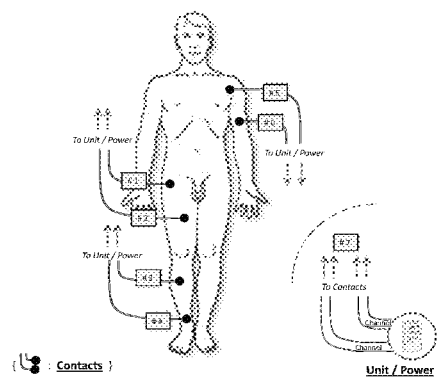

(56) References Cited

U.S. PATENT DOCUMENTS

| | | | |
|---|---|---|---|
| 7,206,632 B2* | 4/2007 | King | A61N 1/36021 |
| | | | 600/544 |
| 7,424,325 B2* | 9/2008 | Koller | A61F 6/04 |
| | | | 607/143 |
| 7,868,072 B2 | 1/2011 | Sasahara et al. | |
| 7,991,476 B2* | 8/2011 | Nachum | A61N 1/36003 |
| | | | 607/48 |
| 8,204,607 B2* | 6/2012 | Rooney | A61N 1/0531 |
| | | | 607/130 |
| 8,260,439 B2* | 9/2012 | DiUbaldi | A61N 1/0456 |
| | | | 607/145 |
| 8,343,147 B2 | 1/2013 | Rosemberg | |
| 8,428,735 B2 | 4/2013 | Littlewood et al. | |
| 8,612,008 B2 | 12/2013 | Kirsch et al. | |
| 8,633,229 B2 | 1/2014 | Bhaskaran et al. | |
| 8,758,215 B2 | 6/2014 | Legendre et al. | |
| D716,457 S | 10/2014 | Brefka et al. | |
| 8,876,696 B2 | 11/2014 | Mikhailenok et al. | |
| 8,883,741 B2 | 11/2014 | Myasoedov et al. | |
| 8,897,877 B2* | 11/2014 | Forward | A61N 1/0492 |
| | | | 607/39 |
| 8,948,876 B2 | 2/2015 | Gozani et al. | |
| 8,948,879 B2 | 2/2015 | Turner et al. | |
| 8,954,153 B2 | 2/2015 | Boggs, II | |
| 8,958,883 B2 | 2/2015 | Mueller et al. | |

OTHER PUBLICATIONS

Roscoe Medical, Current Solutions Product Catalog, states "(c) 2013", "Twin Stim" mentioned at pp. 3 and 14.

* cited by examiner

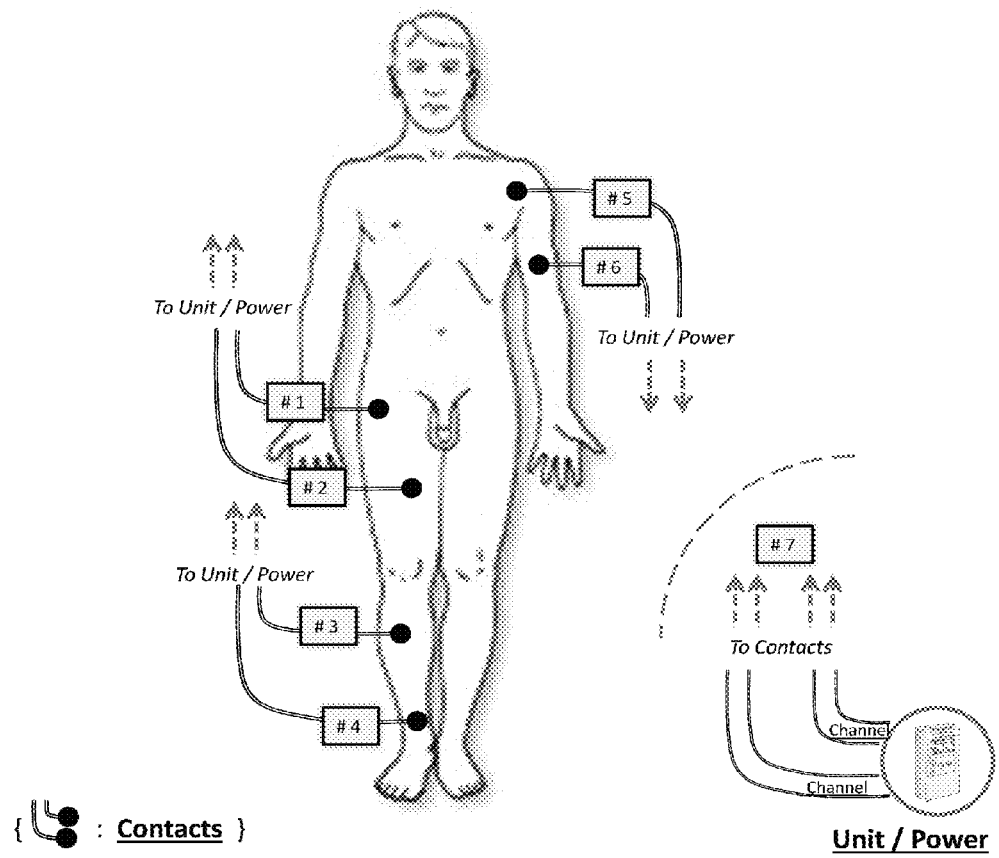

Figure # 1. - Three Channels (two Contacts per Channel) to the "Unit / Power".

Legend:
- #1: Channel No. 1 - Contact and wire from right-hip area to the Unit / Power.
- #2: Channel No. 1 - Contact and wire from right-thigh area to the Unit / Power.
- #3: Channel No. 2 - Contact and wire from right-top-shin area to the Unit / Power.
- #4: Channel No. 2 - Contact and wire from right-bottom-shin area to the Unit / Power.
- #5: Channel No. 3 - Contact and wire from left-shoulder area to the Unit / Power.
- #6: Channel No. 3 - Contact and wire from left-bicep area to the Unit / Power.
- #7: Wires from the Unit / Power to the Contacts (two Contacts per one channel).

Figure # 2. - Three Channels (two Contacts per Channel) to the "Unit / Power".

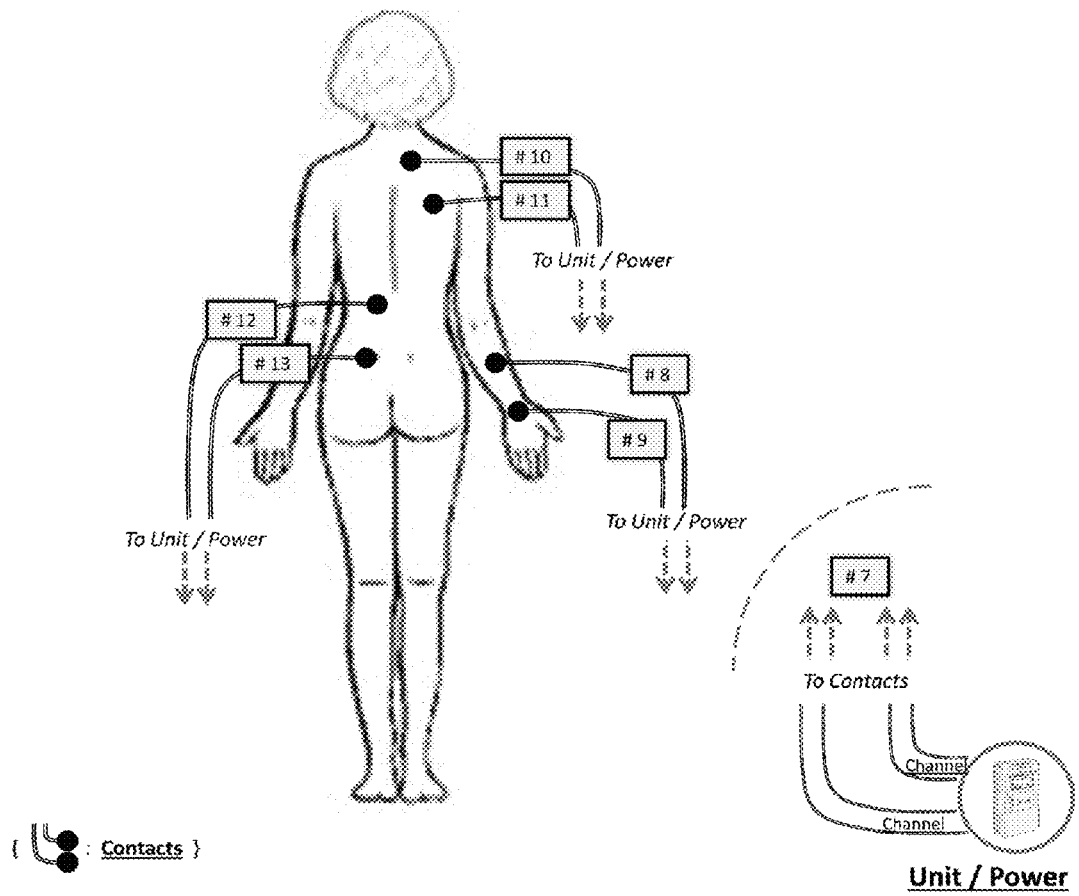

Legend:
- # 7: Wires from the Unit / Power to the Contacts (two Contacts per one channel).
- # 8: Channel No. 4 - Contact and wire from right-back-forearm area to the Unit / Power.
- # 9: Channel No. 4 - Contact and wire from right-back-forearm-wrist area to Unit / Power.
- # 10: Channel No. 5 - Contact and wire from right-upper-back area to the Unit / Power.
- # 11: Channel No. 5 - Contact and wire from right-mid-back area to the Unit / Power.
- # 12: Channel No. 6 - Contact and wire from left-mid-back area to Unit / Power.
- # 13: Channel No. 6 - Contact and wire from left-lower-back area to Unit / Power.

Figure # 3. - The "Unit / Power" to Contacts Wire (two Contacts per Channel).

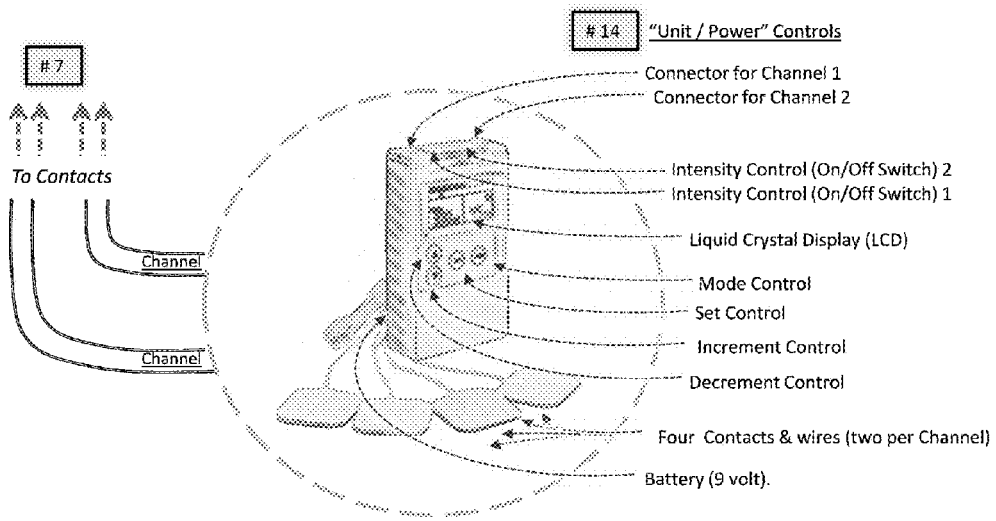

Legend:
7: Wires from the Unit / Power to the Contacts (two Contacts per area).
14: Unit / Power Controls, Contacts, Wires; basic TENS/EMS unit controls listed.

Unit / Power Unit:
- A standard TENS/EMS Unit. Patents exist for TENS/EMS technology.
- The Twin-Stim unit is a dual unit; four contacts, for two channels. One to four channels (even more) are available on different models. Twin Stim Manual URL: http://www.currentsolutionsnow.com/images/highresolution/TWINSTIM.pdf
- Depending on units, power could come from batteries (AA or 9 Volt), recharging batteries, lithium batteries, or AC outlet.
- Battery powered allows you to move around during sessions, using the belt-clip.

ELECTRONIC PROCESS TO RESTORE, IMPROVE AND/OR STRENGTHEN THE LIBIDO; METHOD TO MEND THE SEX DRIVE IN MALES AND FEMALES

CROSS/REFERENCE TO (ANY) RELATED APPLICATIONS

None.

FEDERAL RESEARCH SPONSORSHIP (IF ANY) STATEMENT

None.

REFERENCE TO (ANY) SEQUENCE LISTING

None.

TABLE OR COMPUTER PROGRAM LISTING (IF ANY) APPENDIX

None

FIELD

Embodiments of the invention generally pertain to the field of treating medical conditions using TENS/EMS (Transcutaneous Electric Nerve Stimulation/Electronic Muscle Stimulation) technology.

BACKGROUND

TENS/EMS technology existed at least as early as the late 1980's. TENS/EMS units have been prescribed for, for example, chronic back spasms. Non-invasive Electro Pharmaceutical Device (EPD) technology has been developed used and Dr. Saul Liss and his company "Medi Consultants, Inc." for treating depression, headache, fibromyalgia, chronic back pain, TMJ syndrome, cerebral palsy spasticity, and a type of anxiety. Electrotherapy stimulation technology is discussed in U.S. Pat. No. 8,612,008 B2, titled "MICROCURRENT AND CRANIAL ELECTROTHERAPY STIMULATOR FOR CONTROL OF ANXIETY, INSOMNIA, DEPRESSION AND PAIN," which is hereby incorporated by reference. However, the prior art is lacking methods for using TENS/EMS technology that improve the libido with the efficacy of the present invention.

BRIEF SUMMARY

Embodiments of the invention are generally directed to methods for improving the libido using electrical stimulation. According to various embodiments of the invention, electrical stimulation can be applied to the body using a TENS/EMS device, 2, 3 or 4 times a day. According to certain embodiments of the invention, each of these applications occurs for 20 minutes.

BRIEF DESCRIPTION OF THE DRAWINGS

FIG. 1 shows a male front diagram showing placements of electrodes according to embodiments of the present invention.

FIG. 2 shows a female back diagram showing placements of electrodes according to embodiments of the present invention.

FIG. 3 shows exemplary functionality of one possible TENS/EMS unit that may be used according to embodiments of the present invention.

DETAILED DESCRIPTION

According to embodiments of the present invention, acupuncture treatments may be used along with a TENS/EMS unit, for example, on patients who have suffered stroke paralyses.

According to embodiments of the present invention, a TENS/EMS unit may be used for 20 minutes twice per day.

Around the second week of using the TENS/EMS unit a slight improvement in sex drive may occur, a positive increase in the libido. Accordingly to further embodiments of the present invention, use of the TENS/EMS unit can be increased. For example, the TENS/EMS unit may be used for three-or-four 20-minute sessions daily. An individual 20 minute session at home may employ an hour for prepping/treatment/shut-down, on a bed or couch. The libido may continue to improve. According to embodiments of the present invention, the patient may stop getting acupuncture sessions, for example, nine months after commencing use of the TENS/EMS unit, but may keep using the TENS/EMS unit at home, for three-or-four 20-minute sessions per day.

As will be understood by one of ordinary skill in the art, according to embodiments of the present invention, a doctor can select the areas on the patient's body at which the contacts (also known as electrodes) are to be placed.

According to embodiments of the present invention, no other prescriptions, technology, diet, or environment changes are introduced during the treatment period. This allows for monitoring and understanding the progress of the sex drive improvements of TENS/EMS treatments. The basic Project Management Institute's (PMI) project methodology may be employed.

According to embodiments of the present invention, the libido, i.e., sex drive, may return. According to embodiments of the present invention, the patient can have regular sex, for example, at 62 years old. According to embodiments of the present invention, the libido improvement process of embodiments of the present invention can take a calendar time of one year and eight months.

There are Three Drawings:
FIG. 1.) Male front diagram
FIG. 2.) Female back diagram
FIG. 3.) Functionality of the power unit.

Choosing a male or a female for the diagrams has no significance or meaning, regarding the genders illustrated. Exemplary placement of contacts is shown for potentially six channels, while the maximum channels of the unit may be two channels. The potential placement for 12 channels (left & right) locations can be extrapolated.

1.) Male Front Diagram:

There is a front diagram of a male, and the power unit. There are three areas of the body illustrated, where two contacts (also referred to as electrodes) are stuck to the body, with moisture, to the skin. Wires are connected to the contacts. The wires illustrate that they go to the power unit. Every channel, going between the contacts and power unit, preferably includes two wires (positive/negative) to the power unit. The three channel's wires, going to the three areas illustrated, include the right-hip-and-thigh area, the right-top-and-bottom-shin area, and the left-shoulder-and-bicep area.

2.) Female Back Diagram:

There is a back diagram of a female, and the power unit. There are three areas of the body illustrated, where two contacts are stuck to the body, with moisture, to the skin. Wires are connected to the contacts. The wires illustrate that they go to the power unit. Every channel, going between the contacts and power unit, preferably includes two wires (positive-and-negative) to the power unit. The three channel's wires, going to the three areas illustrated, include the right-back-forearm-and-wrist area, the right-upper-and-midback area, and the left-mid-back-and-left-lower-back area.

3.) Functionality of the Power Unit Diagram:

There is a diagram of the power unit. Wires are shown that they are connected to the contacts. The wires illustrate that they go to the power unit. Every channel, going between the contacts and power unit, preferably includes two wires (positive/negative) to the power unit. The basic TENS/EMS unit controls are listed.

Embodiments of this invention can provide a method to improve and strengthen the libido, the sex drive, in males and females, without introducing any external or unnatural drugs.

The method can provide a TENS/EMS power source, two electrodes, wiring, and optionally additional electrodes. TENS/EMS units typically have no side effects other than possible skin irritation (where the electrodes are placed on the skin; if the machine is left on too long). Some form of cream, or lubrication, could be beneficial.

The process utilizes a TENS/EMS (Transcutaneous Electrical Nerve Stimulation/Electronic Muscle Stimulation) machine to naturally generate the increased production by the human body's nerve fiber's neurotransmitters. The TENS/EMS unit produces electric currents to stimulate the nerves. The pulses produced by stimulators are used for nerve excitation. The unit is able to modulate pulse width, frequency and intensity. Generally TENS is applied at high frequency (>50 Hz) with an intensity below motor contraction (sensory intensity) or low frequency (<10 Hz) with an intensity that produces contractions.

Here are exemplary adjustable specifications of a Twin-Stim TENS/EMS unit that can be used:

Pulse Amplitude: Adjustable, 0-100 mA peak into 500 ohm load each channel.
Voltage 0 to 50V (Load: 500 ohm)
Pulse Rate Adjustable, from 2 to 150 Hz, 1 Hz-step
Pulse Width Adjustable, from 50 to 300 microseconds
On Time Adjustable (Contraction Time), 2-90 seconds, 1 Sec.-step
Off Time Adjustable (Relaxation Time), 2-90 seconds, 1 Sec.-step
Ramp Time Adjustable, 1-8 seconds, 1 Sec.-step
Five TENS Modes: B (Burst), N(Normal), M (Modulation), SD1 (Strength Duration), SD2
Two EMS Modes: S(Synchronous), A (Alternate)
10 Burst Mode Burst rate: Adjustable, 0-5-5 Hz
Pulse width adjustable, 50-300 uS
Frequency fixed=100 Hz.

The settings should preferably be set-up by a professional/doctor. There are standards and average settings available on the internet, but professionals can set-up units based on experience, the person's needs, different physical sizes and compositions.

The company "Current Solutions LLC" sells a TENS/EMS unit that may be used according to embodiments of the present invention.

One exemplary model is "Twin Stim® TENS and EMS Combo".

Additional Product Features:

System includes device, lead wires, four self-adhesive reusable electrodes, 9-volt battery, hard plastic carrying case and instruction manual
Patient compliance meter can store up to 60 sets of operation records and 999 hours
Power Source: 9-volt battery
Wave Form: Asymmetrical Bi-Phase Square Pulse
Timer: 1-60 minutes or continuous.

The Food and Drug Administration's (FDA) rules must be complied with; followed for manufacturing, sales, and purchasing TENS/EMS units. This is a Class II Medical device. Federal law may restrict TENS/EMS devices to the sale of units by or on the order of a licensed health care professional.

When the unit has been set-up, time should be allowed for three or four sessions a day, faithfully. The patient can consider walking around with the unit hooked up and running, but according to another embodiment, that is not done. It can work better when the patient can lie down or lounge for the session. When the patient moves around with unit on, the electrodes can get pulled off, the unit can fall off, and if the patient is not dressed properly the patient must typically partially undress.

There may be slight feelings of the patient's libido, his or her sex drive, improving within weeks. The patient's libido will continue to improve as months progress. The first feelings will happen in the early morning. Men may wake with an erection. Women may also get (clitoral) erections during sleep. According to embodiments of the present invention, the same methods may be employed for men and women.

The feelings, or erections, continue to increase. The ability increases as the TENS/EMS sessions continue. It continues, getting stronger over time, until the ability to reach a climax returns. After numerous months, the patient may reach a climax, which may be repeatable a few weeks later. The time to reach a climax takes a long time, at first. The time required to reach a climax takes shorter and shorter amount of time. After numerous months later, the client may regain the ability to reach a climax every day or two.

The libido, the sex drive, may return. According to embodiments of the present invention, the calendar time that this process may take may be one year and eight months.

What is claimed is:

1. A method for increasing a sex drive of a person, comprising:
   providing a regimen using a transcutaneous electrical nerve stimulation/electronic muscle stimulation (TENS/EMS) apparatus, the regimen including:
      placing a plurality of electrodes of the TENS/EMS apparatus on a plurality of locations on the person's body, the plurality of electrodes comprising at least one pair of paired electrodes; and
      administering electrical stimulation to the person's body via the plurality of electrodes,
      wherein the regimen is performed three or four times within a 24 hour period and wherein the electrical stimulation is administered for approximately twenty minutes during each of the three or four times.

2. The method of claim 1, wherein the regimen is performed three times within a 24 hour period.

3. The method of claim 1, wherein the regimen is performed four times within a 24 hour period.

4. The method of claim 1, wherein a first electrode of the pair of paired electrodes is placed on a hip area of the body and a second electrode of the pair of paired electrodes is placed on a thigh area of the body.

5. The method of claim 1, wherein a first electrode of the pair of paired electrodes is placed on a shoulder area of the body and a second electrode of the pair of paired electrodes is placed on a bicep area of the body.

6. The method of claim 1, wherein a first electrode of the pair of paired electrodes is placed on a forearm area of the body and a second electrode of the pair of paired electrodes is placed on a wrist area of the body.

7. The method of claim 1, wherein a first electrode of the pair of paired electrodes is placed on an upper-back area of the body and a second electrode of the pair of paired electrodes is placed on a mid-back area of the body.

8. The method of claim 1, wherein a first electrode of the pair of paired electrodes is placed on a mid-back area of the body and a second electrode of the pair of paired electrodes is placed on a lower back area of the body.

9. The method of claim 1, wherein the regimen is unaccompanied by drugs for the increasing of the sex drive of the person.

10. The method of claim 1, wherein the regimen is administered for a period of at least one year.

11. The method of claim 1, wherein the regimen is administered for a period of approximately One year and eight months.

12. The method of claim 1, wherein the plurality of electrodes consist of the one pair of paired electrodes.

13. The method of claim 1, wherein the plurality of electrodes consist of the one pair of paired electrodes and one additional pair of paired electrodes.

14. The method of claim 13, wherein the one pair of paired electrodes and the one additional pair of paired electrodes are placed at different pairs of locations on the person's body selected from the group consisting of hip area and thigh area, top-shin area and bottom-shin area, should area and bicep area, forearm area and wrist area, upper-back area and mid-back area, and mid-back area and lower back area.

15. The method of claim 1, wherein the plurality of electrodes consist of the one pair of paired electrodes and a first additional pair of paired electrodes and a second additional pair of paired electrodes.

16. The method of claim 15, wherein the one pair of paired electrodes, the first additional pair of paired electrodes, and the second additional pair of paired electrodes are placed at different pairs of locations on the person's body selected from the group consisting of hip area and thigh area, top-shin area and bottom-shin area, should area and bicep area, forearm area and wrist area, upper-back area and mid-back area, and mid-back area and lower back area.

17. The method of claim 1, wherein the method is for treating an inadequate sex drive diagnosed as being caused by stroke paralysis.

18. The method of claim 1, wherein the regimen is performed on a person undergoing acupuncture sessions.

19. The method of claim 1, wherein the regimen is performed on a person undergoing acupuncture sessions for a period of approximately nine month following the start of the regimen and then discontinuing acupuncture but continuing with the regimen.

20. The method of claim 1, wherein the person is a nude.

21. The method of claim 1, wherein the person is a female.

22. The method of claim 1, wherein the method results in a return of an ability for the person to reach a climax.

* * * * *